United States Patent
Iwanaka et al.

(10) Patent No.: US 10,304,187 B2
(45) Date of Patent: May 28, 2019

(54) IMAGE PROCESSING APPARATUS AND METHOD, COMPUTER PROGRAM PRODUCT, AND STEREOSCOPIC IMAGE DISPLAY APPARATUS

(71) Applicant: Toshiba Medical Systems Corporation, Otawara-shi (JP)

(72) Inventors: Yuki Iwanaka, Ota (JP); Takeshi Mita, Yokohama (JP); Yoshiyuki Kokojima, Yokohama (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 707 days.

(21) Appl. No.: 14/948,588

(22) Filed: Nov. 23, 2015

(65) Prior Publication Data

US 2016/0078620 A1    Mar. 17, 2016

Related U.S. Application Data

(63) Continuation of application No. PCT/JP2014/072025, filed on Aug. 22, 2014.

(30) Foreign Application Priority Data

Aug. 23, 2013   (JP) .................. 2013-173883

(51) Int. Cl.
  *G06T 7/00*   (2017.01)
  *H04N 13/264*   (2018.01)
  (Continued)

(52) U.S. Cl.
  CPC .............. *G06T 7/0014* (2013.01); *A61B 6/12* (2013.01); *A61B 6/461* (2013.01); *A61B 6/466* (2013.01);
  (Continued)

(58) Field of Classification Search
  USPC .............. 382/128, 154; 348/42, 47
  See application file for complete search history.

(56) References Cited

U.S. PATENT DOCUMENTS 5,383,013 A * 1/1995 Cox ...................... G06T 7/593
                                                   356/2
7,035,450 B1 * 4/2006 Muller ................ G06K 9/3233
                                                   382/128
(Continued)

FOREIGN PATENT DOCUMENTS

JP       8-10246       1/1996
JP    2001-153633 A    6/2001
(Continued)

OTHER PUBLICATIONS

Office Action dated Oct. 3, 2017 in Japanese Patent Application No. 2013-173883.

(Continued)

*Primary Examiner* — Ishrat I Sherali
(74) *Attorney, Agent, or Firm* — Oblon, McClelland, Maier & Neustadt, L.L.P.

(57) ABSTRACT

According to an embodiment, an image processing apparatus includes an acquirer, first and second calculators, and a selector. The acquirer acquires a first image of an object captured in a first imaging direction and a second image of the object captured in a second imaging direction. The first calculator calculates, for each pixel included in the respective first and second images, likelihood of whether the pixel is included in a region of the object on the basis of feature information indicating image feature. The second calculator calculates, on the basis of the likelihood, a degree of similarity between a region of interest in the first image and a candidate region in the second image. The candidate region is a candidate of a corresponding region corresponding to the region of interest. The selector selects the candidate region serving as the corresponding region on the basis of the degree of similarity.

13 Claims, 11 Drawing Sheets

(51) Int. Cl.

| | | |
|---|---|---|
| A61B 6/00 | (2006.01) | |
| H04N 5/32 | (2006.01) | |
| A61B 6/12 | (2006.01) | |
| G06T 7/33 | (2017.01) | |
| G06T 7/73 | (2017.01) | |
| H04N 13/211 | (2018.01) | |
| H04N 13/221 | (2018.01) | |
| H04N 13/254 | (2018.01) | |
| H04N 13/111 | (2018.01) | |
| H04N 13/349 | (2018.01) | |
| H04N 13/398 | (2018.01) | |
| A61B 6/02 | (2006.01) | |
| H04N 13/00 | (2018.01) | |

(52) U.S. Cl.
CPC ............ *A61B 6/469* (2013.01); *A61B 6/485* (2013.01); *A61B 6/487* (2013.01); *A61B 6/504* (2013.01); *A61B 6/5211* (2013.01); *A61B 6/5235* (2013.01); *A61B 6/54* (2013.01); *G06T 7/0012* (2013.01); *G06T 7/337* (2017.01); *G06T 7/74* (2017.01); *H04N 5/32* (2013.01); *H04N 13/111* (2018.05); *H04N 13/211* (2018.05); *H04N 13/221* (2018.05); *H04N 13/254* (2018.05); *H04N 13/264* (2018.05); *H04N 13/349* (2018.05); *A61B 6/022* (2013.01); *G06T 2207/10012* (2013.01); *G06T 2207/10116* (2013.01); *G06T 2207/10121* (2013.01); *G06T 2207/20076* (2013.01); *G06T 2207/20224* (2013.01); *G06T 2207/30021* (2013.01); *G06T 2207/30101* (2013.01); *H04N 13/398* (2018.05); *H04N 2013/0074* (2013.01); *H04N 2013/0081* (2013.01)

(56) References Cited

U.S. PATENT DOCUMENTS

| | | | |
|---|---|---|---|
| 7,269,241 B2 | 9/2007 | Siltanen et al. | |
| 8,144,974 B2 | 3/2012 | Masuda | |
| 8,150,132 B2 | 4/2012 | Nakamura | |
| 8,548,226 B2* | 10/2013 | Sakano | G06T 7/593 382/104 |
| 8,649,599 B2 | 2/2014 | Yamada | |
| 8,867,825 B2* | 10/2014 | Ostermann | G06K 9/00986 382/154 |
| 9,478,037 B2* | 10/2016 | Reif | G06F 3/017 |
| 9,774,841 B2* | 9/2017 | Yahagi | H04N 13/0203 |
| 2006/0104406 A1* | 5/2006 | Siltanen | A61B 6/032 378/4 |
| 2007/0031037 A1* | 2/2007 | Blake | G06K 9/00234 382/173 |
| 2007/0211849 A1 | 9/2007 | Movassaghi et al. | |
| 2013/0083894 A1* | 4/2013 | Niebler | A61B 6/4441 378/62 |
| 2014/0043444 A1 | 2/2014 | Haraguchi et al. | |
| 2015/0256813 A1* | 9/2015 | Dal Mutto | H04N 13/254 348/47 |
| 2016/0078620 A1* | 3/2016 | Iwanaka | H04N 5/32 600/424 |

FOREIGN PATENT DOCUMENTS

| | | |
|---|---|---|
| JP | 2003-204483 | 7/2003 |
| JP | 2005-536308 | 12/2005 |
| JP | 2007-515985 | 6/2007 |
| JP | 2009-205193 | 9/2009 |
| JP | 2009-219655 | 10/2009 |
| JP | 2011-34178 | 2/2011 |
| JP | 2011-90465 | 5/2011 |
| JP | 2011-180675 | 9/2011 |
| JP | 2012-208759 | 10/2012 |
| JP | 2012-247364 A | 12/2012 |
| JP | 2013-12045 | 1/2013 |
| JP | 2013-76621 A | 4/2013 |

OTHER PUBLICATIONS

English translation of the Written Opinion dated Nov. 25, 2014 in PCT/JP2014/072025 filed Aug. 22, 2014.

International Search Report dated Nov. 25, 2014 in PCT/JP2014/072025, filed Aug. 22, 2014 (with English Translation).

Written Opinion dated Nov. 25, 2014 in PCT/JP2014/072025, filed Aug. 22, 2014.

Jaesik Park et al. "High Quality Depth Map Upsampling for 3D-TOF Cameras", 2011 IEEE International Conference on Computer Vision, 2011, 8 pages.

* cited by examiner

FIG.9
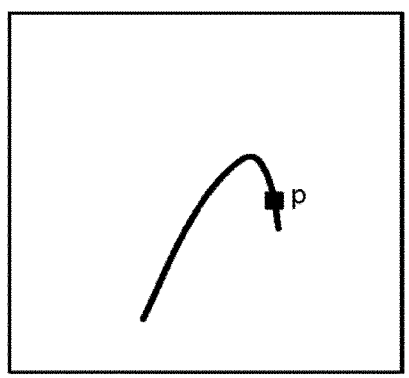
BASE IMAGE
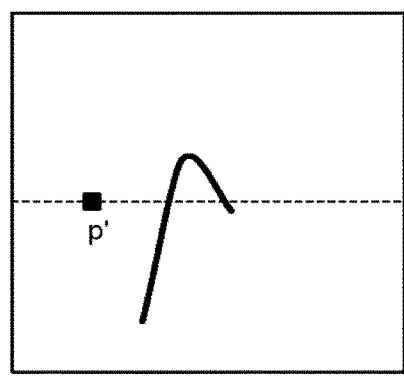
REFERENCE IMAGE
FIG.10
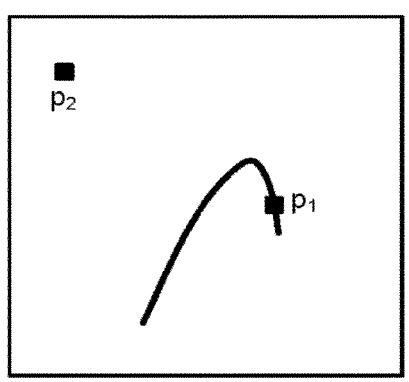
BASE IMAGE
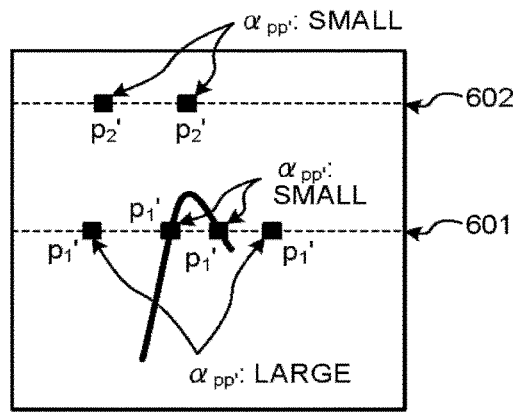
REFERENCE IMAGE

IMAGE PROCESSING APPARATUS AND METHOD, COMPUTER PROGRAM PRODUCT, AND STEREOSCOPIC IMAGE DISPLAY APPARATUS

CROSS-REFERENCE TO RELATED APPLICATIONS

This application is a continuation of International Application No. PCT/JP2014/072025, filed on Aug. 22, 2014 which claims the benefit of priority of the prior Japanese Patent Application No. 2013-173883, filed on Aug. 23, 2013, the entire contents of which are incorporated herein by reference.

FIELD

An embodiment described herein relates generally to an image processing apparatus and method, a computer program product, and a stereoscopic image display apparatus.

BACKGROUND

Techniques (stereo matching) have been proposed in which the same object is captured using imaging devices placed at different positions and, on the basis of a plurality of captured images, the corresponding points on the object in the respective images are searched for. If an image that is taken by one imaging device and serves as a basis is called a base image and images taken by the other imaging devices are called reference images, the stereo matching means it searches for regions in the reference images corresponding to a region of interest (a region including at least one pixel) in the base image.

In typical stereo matching, a region corresponding to the region of interest in the reference image is searched for by optimizing similarity degrees of image features and continuity of parallax in the whole of the image. Specifically, regions that resemble the region of interest in image feature in the reference image are searched for as candidate regions (optimization of the degree of similarity) and, out of the candidate regions, the candidate region, whose parallax with respect to a pixel (adjacent pixel) adjacent to the region of interest in the base image is continuous, selected as the region corresponding to the region of interest (optimization of continuity). Generally, a pixel value, an SSD (Sum of Squared Differences), or an SAD (Sum of Absolute Differences) is used as the image feature.

As a conventional technique, a method is known in which, when a plurality of points corresponding to a pixel (a pixel of interest) in the base image are retrieved, distance values (interest distance values) between the pixel of interest and the respective corresponding points are calculated, and the corresponding point is selected that minimizes a difference between the interest distance value and the distance values (adjacent distance values) of a plurality of pixels present around the pixel of interest (a first conventional technique). A technique is also known in which the continuity of parallax is not evaluated in a region having a high edge intensity so as not to evaluate the continuity of parallax across the boundary of the object (a second conventional technique). A technique may also be conceivable in which a region of the object is detected by performing segmentation of an image and the corresponding points are retrieved from within the detected region (a third conventional technique).

The first and the second conventional techniques, however, employ a method in which the corresponding point positions are optimized in the whole of an image. As a result, when the region of the object (an object region) in the image is small, the first and the second conventional techniques easily receive an influence of an error (error due to noises, for example) occurring in a background region having a larger region than that of the object region. This causes the corresponding point positions of the object region not to be correctly obtained in some cases.

In the third conventional technique, which employs a method in which the object region is detected by performing segmentation, it is hard to extract the object region in both of the base image and the reference image with high accuracy, thereby causing the corresponding point positions of the object region not to be correctly obtained in some cases.

BRIEF DESCRIPTION OF THE DRAWINGS

FIG. 9 is a schematic diagram illustrating an example of a relation between a region of interest and a candidate region of the embodiment.

FIG. 10 is a schematic diagram to explain a weight in relation to a degree of similarity of the embodiment.

DETAILED DESCRIPTION

According to an embodiment, an image processing apparatus includes a first acquirer, a first calculator, second calculator, and a selector. The first acquirer acquires a first image of an object captured in a first imaging direction and a second image of the object captured in a second imaging direction different from the first imaging direction. The first calculator calculates, for each of a plurality of pixels included in the respective first and second images, likelihood of whether the pixel is included in a region of the object on the basis of feature information indicating image feature. The second calculator calculates, on the basis of the likelihood, a degree of similarity between a region of interest in the first image and a candidate region in the second image. The candidate region is a candidate of a corresponding region corresponding to the region of interest in the first image. The selector selects the candidate region serving as the corresponding region on the basis of the degree of similarity.

An embodiment will be described in detail with reference to the accompanying drawings. The embodiment is applied to an X-ray diagnostic apparatus that performs X-ray fluoroscopy on blood vessels such as coronary arteries. The embodiment, however, is not limited thereto.

Figure 1:
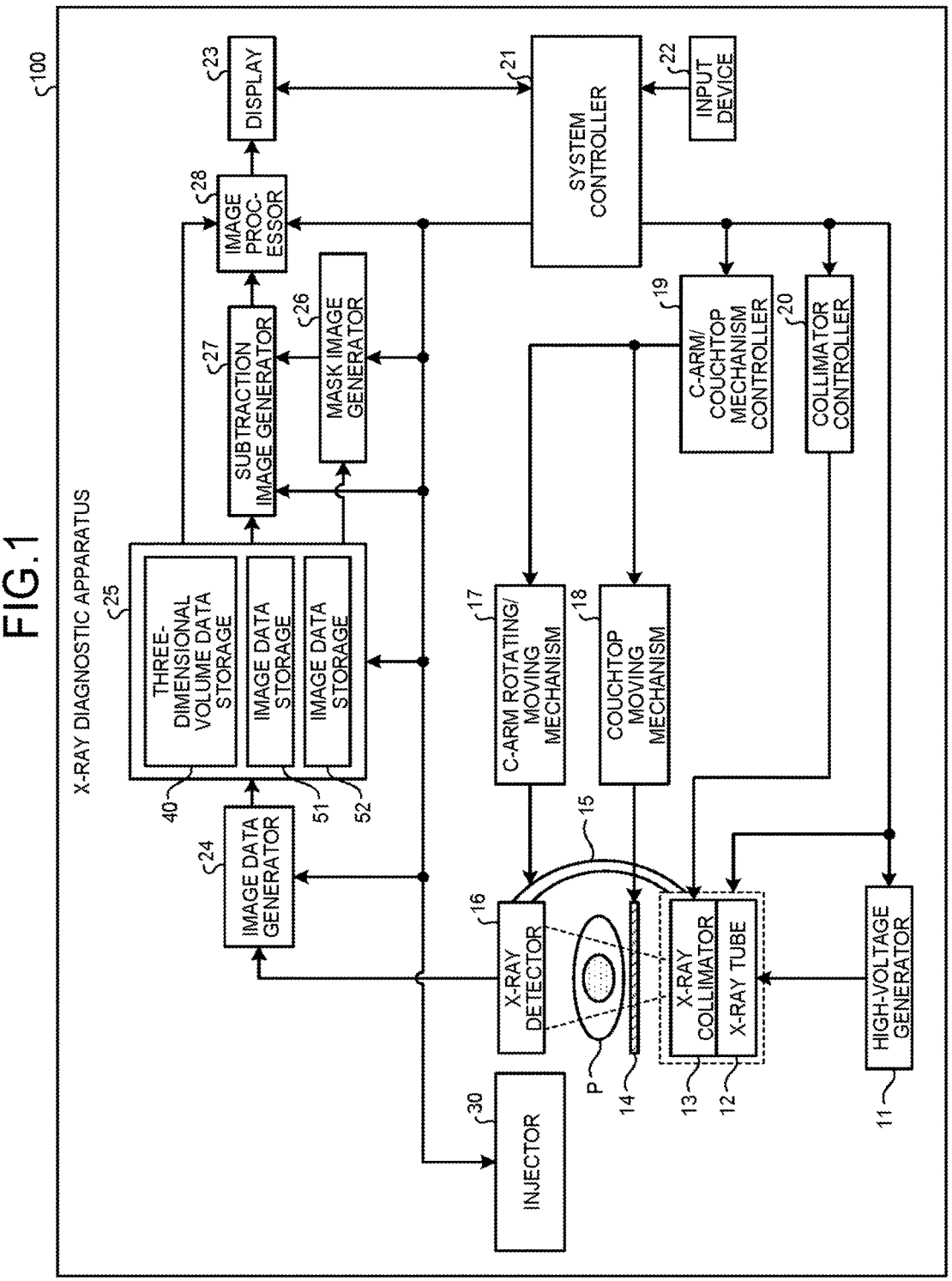
FIG. 1 is a schematic diagram illustrating an exemplary structure of an X-ray diagnostic apparatus of an embodiment.

FIG. 1 is a schematic diagram illustrating an example of a structure of an X-ray diagnostic apparatus 100 according to the embodiment. As illustrated in FIG. 1, the X-ray diagnostic apparatus 100 according to the embodiment includes a high-voltage generator 11, an X-ray tube 12, an X-ray collimator 13, a couchtop 14, a C-arm 15, and an X-ray detector 16. The X-ray diagnostic apparatus 100 also includes a C-arm rotating/moving mechanism 17, a couchtop moving mechanism 18, a couchtop mechanism controller 19, a collimator controller 20, a system controller 21, an input device 22, and a display 23. The X-ray diagnostic apparatus 100 also includes an image data generator 24, a storage 25, a mask image generator 26, a subtraction image generator 27, and an image processor 28. The X-ray diagnostic apparatus 100 further includes an injector 30.

The injector 30 is a device that injects a contrast medium from a catheter (an example of an equipment to be inserted into a blood vessel) inserted into a subject P. The injection of a contrast medium from the injector 30 is performed in accordance with an injection instruction received via the system controller 21, which is described later. Specifically, the injector 30 injects a contrast medium in accordance with an injection start instruction, an injection stop instruction, and contrast medium injection conditions including an injection speed that are received from the system controller 21, which is described later. The injector 30 can start injection in accordance with the injection instruction input by an operator directly to the injector 30 or stop the injection in accordance with the instruction of the operator.

The high-voltage generator 11 generates a high voltage under the control of the system controller 21 and supplies the generated high voltage to the X-ray tube 12. The X-ray tube 12 generates X-rays using the high voltage supplied from the high-voltage generator 11.

The X-ray collimator 13 narrows the X-rays generated by the X-ray tube 12 such that an attention region of the subject P is selectively irradiated with the X-rays under the control of the collimator controller 20. For example, the X-ray collimator 13 has four slidable aperture blades. The X-ray collimator 13 narrows the X-rays generated by the X-ray tube 12 by sliding the aperture blades such that the subject P is irradiated with the narrowed X-rays under the control of the collimator controller 20. The X-ray tube 12 and the X-ray collimator 13 are also collectively called an X-ray tube device. The couchtop 14 is a bed on which the subject P is laid and placed on a couch (not illustrated). The subject P does not belong to the X-ray diagnostic apparatus 100.

The X-ray detector 16 detects X-rays passing through the subject P. For example, the X-ray detector 16 has detection elements arranged in a matrix. The respective detection elements convert X-rays passing through the subject P into electrical signals to accumulate them, and transmit projection data produced on the basis of the accumulated electrical signals to the image data generator 24. For example, the X-ray detector 16 performs current-voltage conversion, analog-digital (A/D) conversion, or a parallel-serial conversion on the accumulated electrical signals to produce the projection image.

It can also be considered that the X-ray tube 12, the X-ray collimator 13, and the X-ray detector 16 correspond to an "X-ray fluoroscopic imaging device" that produces the projection data by performing X-ray fluoroscopy on the subject P.

The C-arm 15 holds the X-ray tube 12, the X-ray collimator 13, and the X-ray detector 16. The X-ray tube 12, the X-ray collimator 13, and the X-ray detector 16 are arranged by the C-arm 15 such that the X-ray tube 12 and the X-ray collimator 13 face the X-ray detector 16 with the subject P interposed therebetween.

The C-arm rotating/moving mechanism 17 is a mechanism that rotates and moves the C-arm 15. The couchtop moving mechanism 18 is a mechanism that moves the couchtop 14. The C-arm/couchtop mechanism controller 19 controls the C-arm rotating/moving mechanism 17 and the couchtop moving mechanism 18 under the control of the system controller 21 to adjust the rotation and the movement of the C-arm 15 and the movement of the couchtop 14. The collimator controller 20 adjusts the opening of the aperture blades of the X-ray collimator 13 under the control of the system controller 21 to control an irradiation range of X-rays with which the subject P is irradiated.

The C-arm/couchtop mechanism controller 19 drives the C-arm rotating/moving mechanism 17 under the control of the system controller 21 to reciprocate and slide the C-arm 15 provided with the imaging system (the X-ray tube 12, the X-ray collimator 13, and the X-ray detector 16) within a certain angular range, thereby making it possible to set two imaging positions (a first imaging position and a second imaging position) preferable to binocular stereo.

Figure 2A:
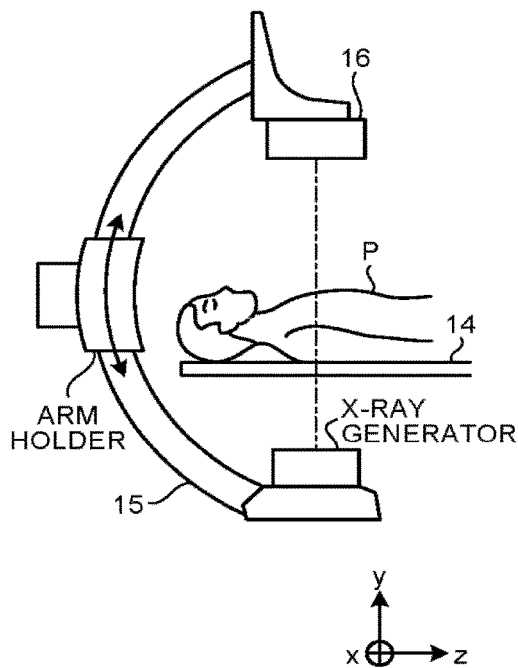
FIGS. 2A and 2B are schematic diagrams to explain a first imaging position and a second imaging position of the embodiment.
Figure 2B:
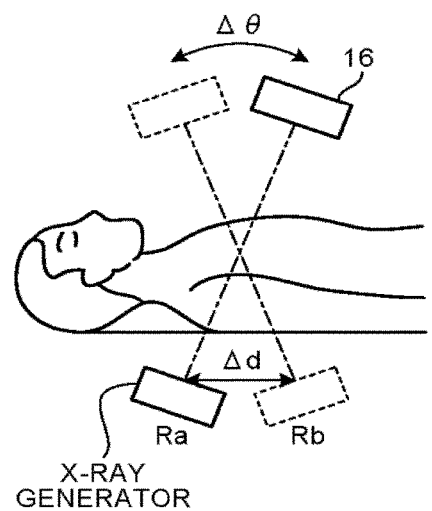

FIG. 2A illustrates directions (arrows) of the reciprocating-sliding movement of the C-arm 15. Near the upper end of the C-arm 15, the X-ray detector 16 is attached. Near the lower end of the C-arm 15, the X-ray tube 12 and the X-ray collimator 13 (hereinafter described as an "X-ray generator" in some cases) are attached. FIG. 2B illustrates a first imaging position Ra (in the following description, described as a "first viewpoint" in some cases) preferable to the binocular stereo and a second imaging point Rb (in the following description, described as a "second viewpoint" in some cases), which are set in the reciprocating-sliding movement. In the following description, an imaging direction at the first imaging position Ra is described as a "first imaging direction" while an imaging direction at the second imaging position Rb is described as a "second imaging direction" in some cases.

The C-arm/couchtop mechanism controller 19 drives the C-arm rotating/moving mechanism 17 under the control of the system controller 21 to cause the C-arm 15 to perform the reciprocating-sliding movement at a high speed within an angle of $\Delta\theta$, resulting in the X-ray generator and the X-ray detector 16 (imaging system) performing the high-speed reciprocating movement around the subject P together with the C-arm 15. As a result, the first imaging position Ra (first viewpoint) and the second imaging point Rb (second viewpoint) are set at turning points, which are separated with a certain imaging distance $\Delta d$, of the high-speed reciprocating movement, for example. The setting of the first and the second viewpoints are not limited thereto.

Referring back to FIG. 1, the image data generator 24 produces the image data on the basis of the projection data supplied from the X-ray detector 16. The image data generator 24 in the embodiment produces the image data corresponding to the first viewpoint (hereinafter described as "first image data" in some cases) on the basis of the projection data supplied from the X-ray detector 16 when the X-ray fluoroscopic operation is performed (when the X-ray fluoroscopic operation in the first imaging direction is performed) at the first viewpoint (first imaging position Ra), and stores the produced first image data in an image data storage 51 included in the storage 25, which is described later. The image data generator 24 produces the image data corresponding to the second viewpoint (hereinafter described as "second image data" in some cases) on the basis of the projection data supplied from the X-ray detector 16 when the X-ray fluoroscopic operation performed (when the X-ray fluoroscopic operation in the second imaging direction is performed) at the second viewpoint (second imaging position Rb), and stores the produced second image data in an image data storage 52 included in the storage 25, which is described later.

The storage 25 stores therein various types of data. In the embodiment, the storage 25 includes a three-dimensional volume data storage 40 and the image data storages 51 and 52.

The three-dimensional volume data storage 40 stores therein a preliminarily produced three-dimensional blood vessel image (volume data of blood vessels) before PCI treatment (before treatment), in which an instrument such as a guide wire or a catheter is inserted into a coronary artery of the heart, for example, and a narrowed portion or a clogged portion of the coronary artery is widened. For example, the X-ray diagnostic apparatus 100 can also collect a plurality of piece of two-dimensional projection data for reconstructing the three-dimensional blood vessel image by digital angiography (DA) imaging or digital subtraction angiography (SSA) imaging, and produce the three-dimensional blood vessel image by reconstructing the collected two-dimensional projection data. The produced three-dimensional blood vessel image can also be stored in the three-dimensional volume data storage 40. The embodiment is not limited thereto. For example, a three-dimensional blood vessel image acquired from an external apparatus (e.g., an X-ray CT apparatus) may be stored in the three-dimensional volume data storage 40.

The digital angiography (DA) imaging is an imaging method that produces a blood vessel angiogram in which blood vessels and organs are enhanced by a contrast medium by digital processing on the basis of information about X-rays detected by the X-ray detector. The digital subtraction angiography (DSA) imaging is an imaging method in which respective image before and after the injection of a contrast medium are produced on the basis of information about X-rays detected by the X-ray detector before the injection of the contrast medium and information about X-rays detected by the X-ray detector after the injection of the contrast medium, and subtracts the image before the injection from the blood vessel angiogram after the injection of the contrast medium, thereby producing an image of only an object (in this example, blood vessels) to which the contrast medium is supplied, by digital processing.

The image data storage 51 stores therein the first image data produced by the image data generator 24. In the image data storage 51, the first image data is collected at certain time intervals and stored in chronological order.

The image data storage 52 stores therein the second image data produced by the image data generator 24. In the image data storage 52, the second image data is collected at certain time intervals and stored in chronological order.

The mask image generator 26 produces the first image data before the PCI treatment (the first image data in a state before an instrument such as a catheter is inserted into the subject P) as a mask image corresponding to the first viewpoint on the basis of the first image data stored in the image data storage 51. The mask image generator 26 also produces the second image data before the PCI treatment as the mask image corresponding to the second viewpoint on the basis of the second image data stored in the image data storage 52.

Figure 3:
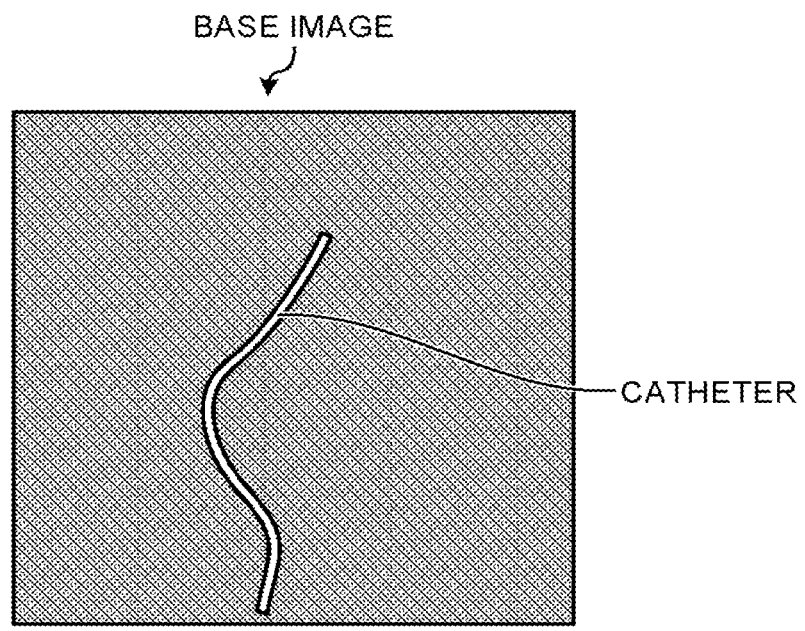
FIG. 3 is a schematic diagram illustrating an example of a base image of the embodiment.

The subtraction image generator 27 produces an image that corresponds to the first viewpoint and in which only an instrument (object) such as a catheter is captured, as illustrated in FIG. 3, (in the following description, described as a "base image" in some cases) by subtracting the mask image corresponding to the first viewpoint produced by the mask image generator 26 from the latest first image data stored in the image data storage 51, when the PCI treatment is performed. The base image is an image of the object captured in the first imaging direction and corresponds to the "first image" in claims. The base image in the embodiment is a subtraction image between the image based on the projection data produced by X-ray fluoroscopy of the subject P in a state where an object is not inserted into a blood vessel in the first imaging direction and the image based on the projection image produced by X-ray fluoroscopy of the subject P in a state where the object is inserted into the blood vessel in the first imaging direction.

Figure 4:
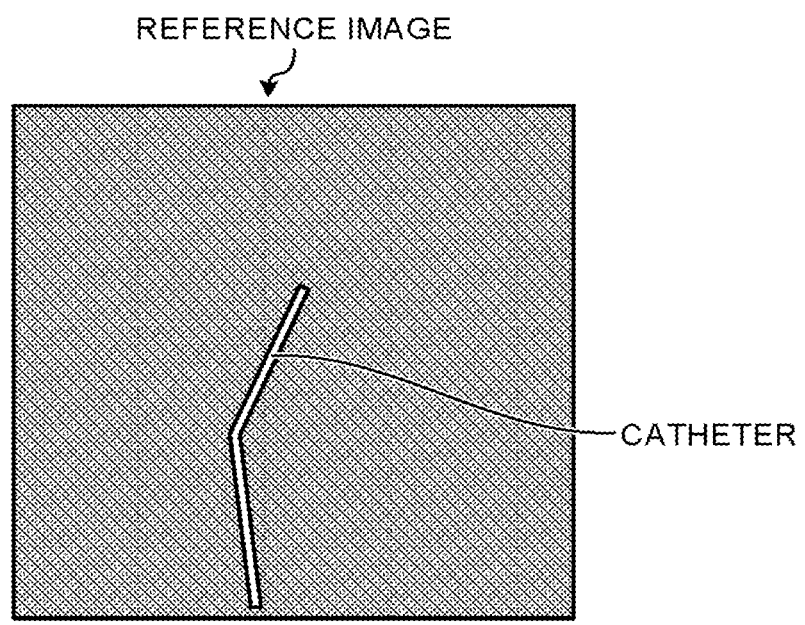
FIG. 4 a schematic diagram illustrating an example of a reference image of the embodiment.

The subtraction image generator 27 produces an image that corresponds to the second viewpoint and in which only the instrument such as a catheter is captured, as illustrated in FIG. 4, (in the following description, described as a "reference image" in some cases) by subtracting the mask image corresponding to the second viewpoint produced by the mask image generator 26 from the latest second image data stored in the image data storage 52. The reference image is an image of the object captured in the second imaging direction and corresponds to the "second image" in claims. The reference image in the embodiment is the subtraction image between the image based on the projection data produced by X-ray fluoroscopy of the subject P in the state where the object is not inserted into the blood vessel in the second imaging direction and the image based on the projection image produced by X-ray fluoroscopy of the subject P in the state where the object is inserted into the blood vessel in the second imaging direction. The base image and the reference image thus produced by the subtraction image generator 27 are supplied to the image processor 28, which is described later.

The image processor 28 performs image processing on the basis of the images supplied from the subtraction image generator 27. For example, the image processor 28 can search for a region (corresponding region) corresponding to a region of interest (region including at least one pixel) of the base image in the reference image and, using the search result, also produce the subtraction image (in this example, an image in which only the instrument such as a catheter is captured, and in the following description, described as an "intermediate image" in some cases) corresponding t a new viewpoint (in the following description, described as an "intermediate viewpoint"). Details of the image processor 28 are described later.

The input device 22 receives various instructions from an operator who operates the X-ray diagnostic apparatus 100 such as a physician or a technician. The input device 22 includes a mouse, a keyboard, buttons, a trackball, and a joystick, for example. The input device 22 transfers an instruction received from an operator to the system controller 21. For example, the input device 22 receives a designation instruction to designate any region in an X-ray image.

The display 23 displays a graphical user interface (GUI) that receives the operator's instruction and the images produced by the image processor 28. The display 23 includes a monitor, for example. The display 23 may include a plurality of monitors.

The system controller 21 is a device that controls the whole of the X-ray diagnostic apparatus 100 on the basis of the operator's operation.

The following describes the image processor 28 according to the embodiment. The image processor 28 according to the embodiment is a device that searches for the region (corresponding region) corresponding to the region of interest of the base image in the reference image on the basis of the base and the reference images described above. The region of interest is a region including at least one pixel.

First, a typical corresponding point search on the basis of energy minimization is described. The corresponding point search is performed to obtain, as a corresponding point position, a region whose image feature resembles that of the region of interest and which causes the parallax of the region of interest and the parallax of a region (adjacent region) adjacent to the region of interest to become close to each other. Specifically, regions whose image features resemble that of the region of interest are determined as candidate regions and the candidate region that causes the parallax of the region of interest and the parallax of the adjacent region to become smooth is select d as the corresponding point position (corresponding region) out of the candidate regions. In a typical corresponding point search technique, an energy is defined as the addition of a degree of similarity between the region of interest and the candidate region and a degree of continuity of the parallax of the region of interest and the parallax of the adjacent region, and the corresponding point positions of the respective regions of interest are searched for in such a way that the energy a minimized in the whole of the image. The degree of similarity is defined by a difference in image features. A pixel value is used as the image feature, for example. The difference in position between the region of interest and the corresponding point is called the parallax. The degree of continuity of parallax is defined by the difference in parallax between the region of interest and the adjacent region. As a result, an energy E is defined by the following expression (1).

$$E = \sum_{p \in P} \|T_B(p) - T_R(p')\| + \sum_{p \in P} \sum_{q \in N(p)} \|D(p) - D(q)\| \quad (1)$$

In expression (1), p represents the region of interest in the base image, p' represents the candidate region that indicates a candidate of the region (corresponding region) corresponding to the region of interest in the reference image, P represents the universal set of the regions of interest in the base image, N(p) represents the universal set of the regions adjacent to the region of interest, $T_B(p)$ represents the pixel value of the region of interest, $T_R(p')$ represents the pixel value of the candidate region, D(p) represents the parallax of the region of interest, and D(q) represents the parallax of the region adjacent to the region of interest. In the right side of expression 1, the first member represents the sum of the degrees of similarity corresponding to the respective regions of interest (a first cost) and the second member represents the sum of the degrees of continuity corresponding to the respective regions of interest (a second cost).

In the energy function expressed by expression (1), of the degrees of similarity and the degrees of continuity of the respective regions of interest are equally evaluated. As a result, when a region of an object (in the following description, described as an "object region" in some cases) included in the image is small, the energy E easily receives the influence of an error occurring in the background image having a larger area than that of the object region. As a result, the corresponding position of the object region is not accurately obtained in some cases. The image processor 28 according to the embodiment thus performs weighting on the basis of likelihood, which is described later, in calculating the first and the second costs, thereby increasing an influence rate (influence rate on the energy function) of the degree of similarity and the degree of continuity corresponding to the region of interest having a high possibility of being included in the object region. As a result, the corresponding point search is performed with high accuracy even when the object region is small. The description is made more specifically below.

Figure 5:
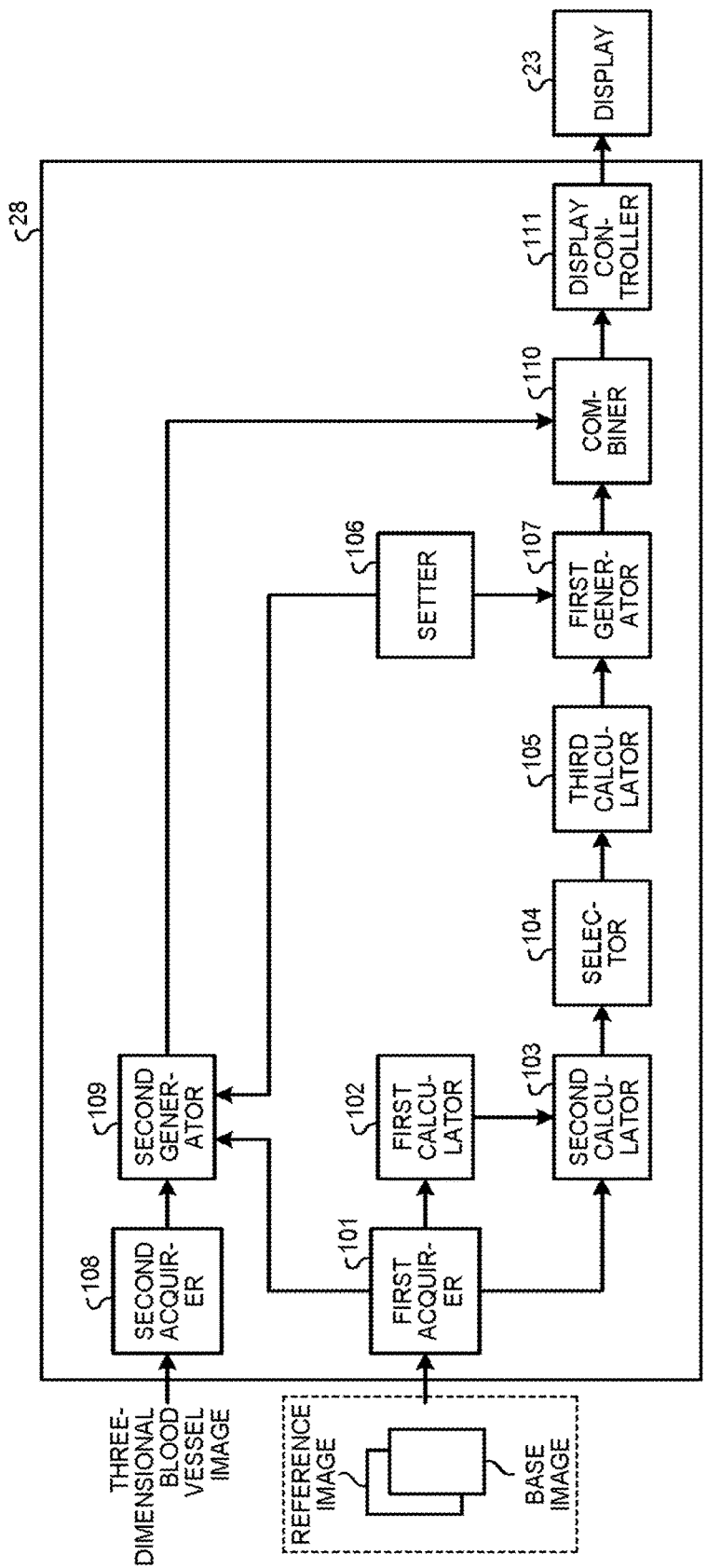
FIG. 5 is a schematic diagram illustrating a structural example of an image processor of the embodiment.

FIG. 5 a block diagram illustrating an example of a structure of the image processor 28 according to the embodiment. As illustrated in FIG. 5, the image processor 28 includes a first acquirer 101, a first calculator 102, a second calculator 103, a selector 104, a third calculator 105, a setter 106, a first generator 107, a second acquirer 108, a second generator 109, a combiner 110, and a display controller 111.

The first acquirer 101 acquires the base and the reference images produced by the subtraction image generator 27. The first acquirer 101 can also acquire information for identifying an epipolar line, which is described later, (e.g., information indicating the fir viewpoint (first imaging position Ra) and the second viewpoint (second imaging point Rb)) from the system controller 21, for example.

The first calculator 102 calculates likelihood of whether the pixel is included in the object region (a degree of possibility of the pixel being included in the object region) for each of a plurality of pixels included in the respective base and reference images on the basis of feature information indicating the features of the images. The first calculator 102 then produces a likelihood map in which the likelihood of all of the pixels is identified. The description is made more specifically below.

Figure 6:
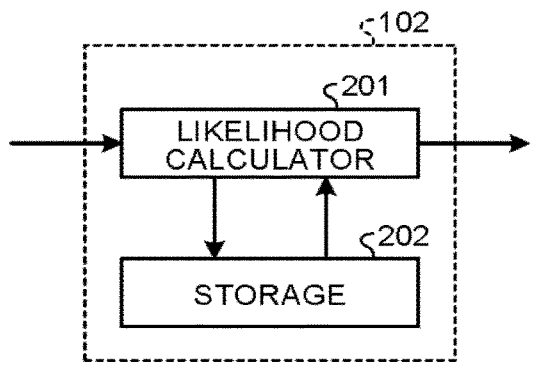
FIG. 6 is a schematic diagram illustrating an example of a detailed structure of a first calculator of the embodiment.

FIG. 6 is a schematic diagram illustrating an example of the detailed structure of the first calculator 102. As illustrated in FIG. 6, the first calculator 102 includes a likelihood calculator 201 and a storage 202. The likelihood calculator 201 calculates the likelihood of the pixel for each of a plurality of pixels included in the respective base and reference images on the basis of a pixel value of the pixel (an example of the "feature information" in claims).

The storage 202 preliminarily stores therein the likelihood corresponding to the pixel value. In this example, the likelihood has continuous values ranging from zero to one. The likelihood having a large value is set for the pixel value of the pixel having a high probability of being included in the object region.

Figure 7:
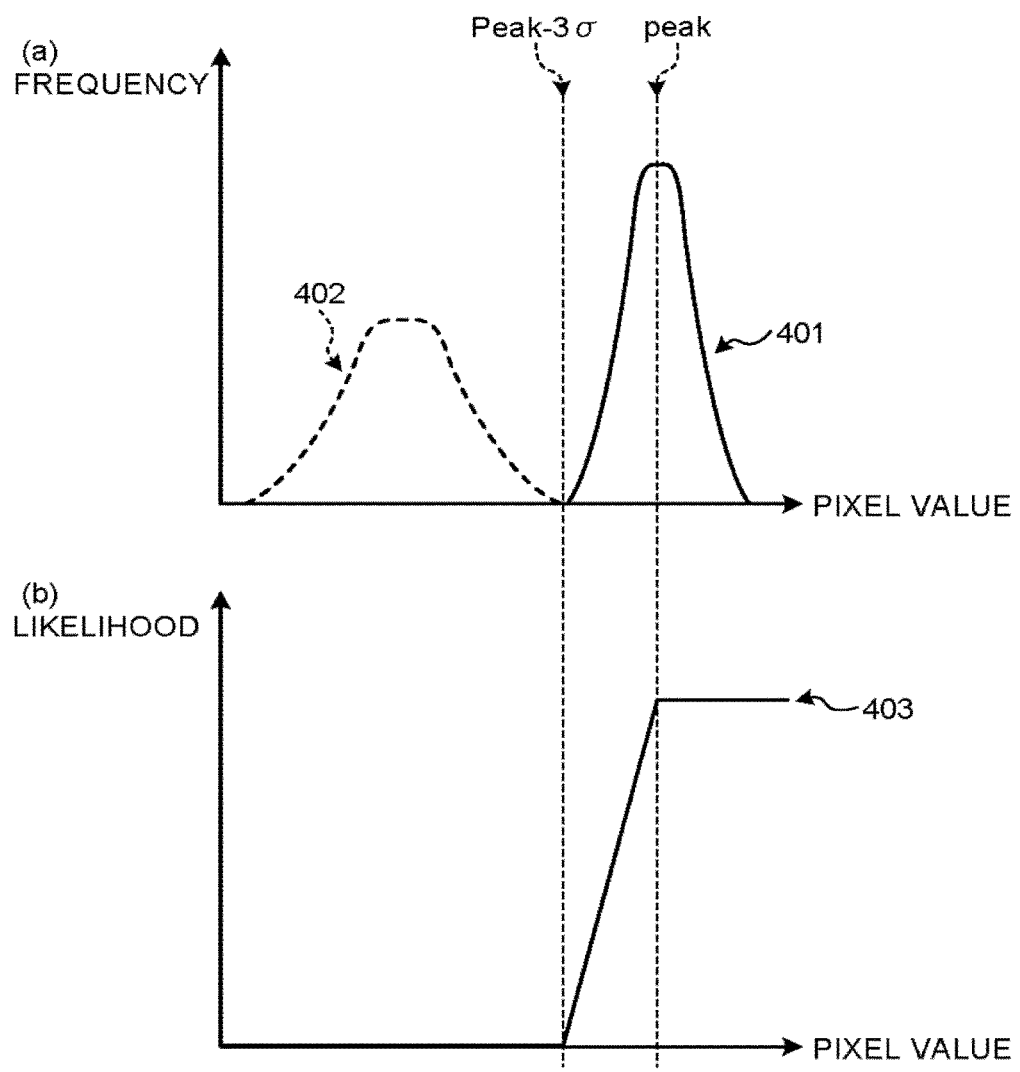
FIG. 7 is a schematic diagram illustrating an example of a relation between a pixel value and likelihood of the embodiment.

FIG. 7 is a schematic diagram to explain an example of a relation between the pixel value and the likelihood. Part (a) in FIG. 7 is a schematic diagram illustrating frequencies of pixel values. An actual line 401 indicates the frequencies of the pixel values of the pixels included in the object region. A broken line 402 indicates the frequencies of the pixel values of the pixels included in the background region. A part (b) in FIG. 7 is a schematic diagram illustrating an example of a likelihood function 403 indicating a relation between pixel value and likelihood. The likelihood is set to one for the pixel value equal to or larger than the pixel value (peak) whose frequency is a maximum out of the pixel values of the pixels in the object region. Assuming that a standard variation of the pixel value distribution of the object region is σ, the likelihood is set to zero for the pixel value equal to or smaller than (peak−3σ), and the likelihood for the pixel value between (peak−3σ) and peak can be obtained by a linear function, connecting (peak−3σ) and peak, expressed by the following expression (2).

$$\text{Likelihood} = \frac{1}{3\delta} \times \text{Image Value} + \frac{3\delta - \text{peak}}{3\delta} \quad (2)$$

In this example, the likelihood function 403 is preliminarily stored in the storage 202. The first calculator 102 calculates the likelihood corresponding to the pixel value of the pixel for each of a plurality of pixels included in the respective base and reference images on the basis of the likelihood function 403. In this way, the first calculator 102 calculates the likelihood of each pixel included in the base and the reference images. The first calculator 102 then produces the likelihood map of the base image that can identify the respective pieces of likelihood of the pixels included in the base image, and the likelihood map of the reference image that can identify the respective pieces of likelihood of the pixels included in the reference image.

In the above description, the likelihood calculator 201 calculates the likelihood on the basis of the pixel value. The embodiment is not limited thereto. For example, the likelihood may be calculated on the basis of the feature information indicating the feature of the image such as a gradient value or a luminance value. When the instrument, such as a catheter or a guide wire, inserted into a blood vessel is the object as described in the embodiment, a region including the blood vessel in the image has a high possibility of being the object region. Thus, the likelihood can also be calculated on the basis of information (e.g., blood vessel information) identifying the object to which the respective pixels in the image belong, for example. In this case, the information such as the blood vessel information corresponds to the "feature information" in claims. For another example, when a "person" is the object, the likelihood can also be calculated on the basis of face feature information (e.g., information indicating respective feature points such as eyes and a nose included in a face, information indicating an outline of the face, and information indicating a skin color) included in the image, for example. In this case, the face feature information corresponds to the "feature information" in claims, for example. For still another example, the likelihood can also be calculated on the basis of user information indicating a region designated by a user as the object region in the image. In this case, the user information corresponds to the "feature information" in claims.

Referring back to FIG. 5, or the second calculator 103, the base and the reference images are input from the first acquirer 101 and the likelihood maps described above are input from the first calculator 102. In this example, the information for identifying the epipolar line, which is described later, (e.g., information indicating the first viewpoint and the second viewpoint) is also input to the second calculator 103 from the first acquirer 101. The second calculator 103 calculates the degree of similarity between the region of interest in the base image and the candidate region, which is a candidate of the corresponding region indicating the region corresponding to the region of interest, in the reference image on the bass of the likelihood of the base and the reference images. More specifically, the second calculator 103 calculates the degree of similarity between the region of interest and the candidate region by weighting the difference in pixel values between the region of interest and the candidate region on the basis of the likelihood of the base and the reference images. The description is made in detail below.

Figure 8:
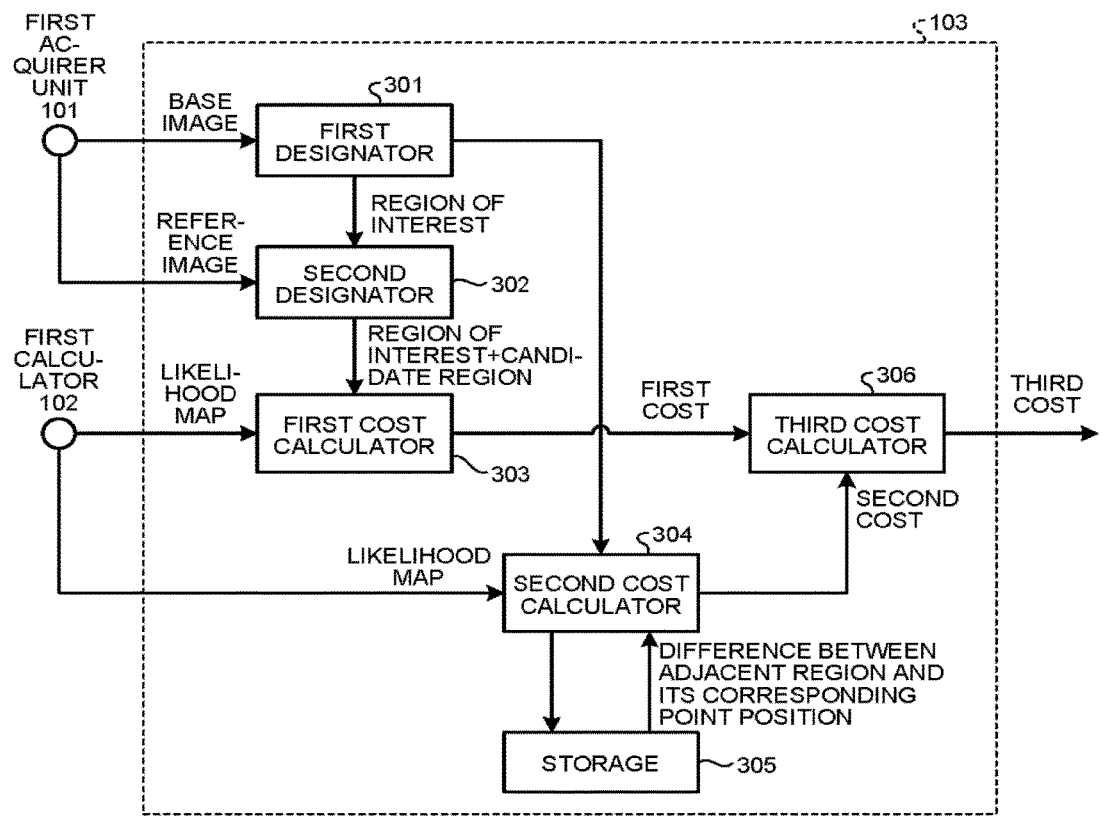
FIG. 8 is a schematic diagram illustrating an example of a detailed structure of a second calculator of the embodiment.

FIG. 8 is a schematic diagram illustrating an example of the detailed structure of the second calculator 103. As illustrated in FIG. 8, the second calculator 103 includes a first designator 301, a second designator 302, a first cost calculator 303, a second cost calculator 304, a storage 305, and a third cost calculator 306.

The first designator 301 designates (sets) the region of interest including at least one pixel in the base image input from the first acquirer 101. More specifically, the first designator 301 designates a plurality of regions of interest included in the base image. In this example, each of a plurality of pixels included in the base image corresponds to the region of interest. The first designator 301 sequentially designates the respective pixels included in the base image (e.g., in the order of raster scan from the upper pixel) as the regions of interest.

The second designator 302 designates, in the reference image, a plurality of regions present on the epipolar line determined on the basis of the position of the region of interest in the base image as the multiple candidate regions corresponding to the region of interest. More specifically, the epipolar line is determined on the basis of a positional relation between the first and the second viewpoints and on the basis of the position of the region of interest in the base image. As described above, the second designator 302 designates multiple candidate regions corresponding to the region of interest for each region of interest designated by the first designator 301. The following specifically describes how the multiple candidate regions corresponding to the region of interest are determined.

FIG. 9 is a schematic diagram illustrating a relation between the region of interest and the candidate region. When a pixel p is designated as the region of interest by the first designator 301, a candidate region p' corresponding to the pixel p is obtained on the epipolar line indicated by a broken line 501. The epipolar line 501 is calculated on the basis of the positional relation between the first and the second viewpoints and on the basis of the position of the pixel p. In the example of FIG. 9, the second designator 302 can also designate all of the pixels on the epipolar line 501 as the candidate regions corresponding to the pixel p.

Referring back to FIG. 4, to the first cost calculator 303, the likelihood maps of the base and the reference images are input from the first calculator 102 and the region of interest and the candidate region are input from the second designator 302. The first cost calculator 303 calculates the degree of similarity by weighting the difference in pixel values between the region of interest and the candidate region on the basis of the likelihood, and calculates the first cost indicating the sum of the degrees of similarity corresponding to the respective regions of interest. The first cost can be calculated by the following expression (3), for example. In this case, the first costs are calculated in number corresponding to the number of combinations of the region of interest and the candidate region.

$$\text{First Cost} = \sum_{p \in P} \|T_B(p) - T_R(p')\| \times \alpha_{pp'} \quad (3)$$

In expression (3), p represents the region of interest, p' represents the candidate region, $T_B(p)$ represents the pixel value of the region of interest, $T_R(p')$ represents the pixel value of the candidate region, and $\alpha_{pp'}$ represent weight relating to the degree of similarity. For example, the value of the weight $\alpha_{pp'}$, which is multiplied by the difference in pixel values between the region of interest and the candidate region, is set to a large value for the region of interest having a high probability (high likelihood) of being included in the object region, thereby also making it possible to greatly reflect the degree of similarity corresponding to the region of interest on an energy (third cost), which is described later. In other words, the first cost calculator 303 (second calculator 103) can also perform weighting (set the weight $\alpha_{pp'}$) such that the higher the possibility of the region of interest being included in the object region is, the larger the weight multiplied by the difference between the pixel values is. In this case, the weight $\alpha_{pp'}$ can also be calculated by the following expression (4), for example.

$$\alpha_{pp'} = L_B(p) \quad (4)$$

In expression (4), $L_B(p)$ represents the likelihood of the region of interest. The weight $\alpha_{pp'}$ expressed by expression (4) has a large value when the probability of the region of interest being included in the object region is high (likelihood is high). In other words, when the probability of the region of interest being included in the object region is high, the weight $\alpha_{pp'}$ is large regardless of the likelihood of the candidate region. In contrast, when the probability of the region of interest being included in the background region is high (the probability of the region of interest being included in the object region is low), the weight $\alpha_{pp'}$ is small regardless of the likelihood of the candidate region.

However, a case is conceivable where the pixel values greatly differ between the region of interest having a high possibility of being included in the object region and the candidate region (having a high possibility of being included in the object region and having a pixel value close to the pixel value of the region of interest) to be determined as the corresponding region due to noises occurring in the image, for example. In such a case, the degree of similarity between the region of interest and the candidate region to be determined as the corresponding region becomes large. As a result, a case occurs where the candidate region does not cause the energy (third cost), which is described later, to be minimized. This may cause the candidate region having a high probability of being included in the background region and having a pixel value close to the pixel value of the region of interest to be selected as the corresponding region instead of the candidate region that should be determined as the corresponding region.

The embodiment solves the problem by setting a small value of the weight $\alpha_{pp'}$ when the possibility of the region of interest and the candidate region being included in the object region is high. In other words, the first cost calculator 303 (second calculator 103) can also perform weighting (set the weight $\alpha_{pp'}$) in such a way that the higher the possibility of the region of interest and the candidate region being included in the object region is, the smaller the weight multiplied by the difference between the pixel values is. The weight $\alpha_{pp'}$ of the embodiment can also be calculated by the following expression (5), for example. The embodiment is not limited thereto. For example, the first cost can be calculated using the weight $\alpha_{pp'}$ expressed by expression (4).

$$\alpha_{pp'} = \sqrt{L_B(p) \times (1 - L_R(p))} \quad (5)$$

In expression (5), $L_R(p')$ represents the likelihood of the candidate region. FIG. 10 is a schematic diagram to explain the weight $\alpha_{pp'}$ expressed by expression (5). In FIG. 10, $p_1$ and $p_2$ represent regions of interest while $p'_1$ and $p'_2$ represent candidate regions. A broken line 601 indicates the epipolar line determined on the basis of the position of $p_1$ while a broken line 602 indicates the epipolar line determined on the basis of the position of $p_2$. In the example of FIG. 10, the region of interest $p_1$ is included in the object region. Thus, the weight $\alpha_{pp'}$ is small when the candidate region is included in the object region. In contrast, the region of interest $p_2$ is included in the background region. Thus, the weight $\alpha_{pp'}$ is small both when the candidate region is included in the object region and when the candidate region is included in the background region.

As described above, the search for the corresponding point the object region can be performed with high accuracy by preferentially adding the degree of similarity of the region of interest having a high possibility of being included in the object region to the energy (third cost), which is described later. As described above, the likelihood has continuous values from zero to one, thus the weight $\alpha_{pp'}$ also has continuous values from zero to one. The degree of similarity is defined as a result of the multiplication of the weight $\alpha_{pp'}$ and the difference in pixel values between the region of interest and any one of the multiple candidate regions corresponding to the region of interest. In the candidate regions corresponding to the region of interest, the larger the degree of similarity is, the larger the weight $\alpha_{pp'}$ is even when the difference in pixel values between the region of interest and the candidate region is the same.

Referring back to FIG. 8, to the second cost calculator 304, the region of interest is input from the first designator 301, the likelihood map of the base image is input from the first calculator 102, and the parallax of the adjacent region (a region adjacent to the region of interest in the base image) is input from the storage 305. The storage 305 preliminarily stores therein the parallax of the adjacent region and outputs the parallax of the adjacent region in accordance with the position of the region of interest.

The second cost calculator 304 calculates the degree of continuity by weighting the difference in parallax between the region of interest and the adjacent region on the basis of the likelihood, and calculates the second cost indicating the sum of the degrees of continuity of parallaxes corresponding to the respective regions of interest. The second cost can be calculated by the following expression (6), for example. In this case, the second costs are calculated in number corresponding to the number of combinations of the region of interest and the candidate region.

$$\text{Second Cost} = \sum_{p \in P} \sum_{q \in N(p)} \|D(p) - D(q)\| \times \beta_{pq} \quad (6)$$

In expression (6), p represents the region of interest, q represents the adjacent region, P represents the universal set of the regions of interest in the base image, N(p) represents the universal set of the adjacent regions, D(p) represents the parallax of the region of interest, D(q) represent the parallax of the adjacent region, and $\beta_{pq}$ represent weight in relation to the degree of continuity. In the embodiment, when the probability of both of the region of interest and the adjacent region being included in the object region is high, the value of the weight $\beta_{pq}$, which is multiplied by the difference in parallax between the region of interest and the adjacent regions is set to a large value. This makes it possible to greatly reflect the degree of continuity of parallax in the object region on the energy (third cost), which is described later. In other words, the second cost calculator 304 (second calculator 103) can also perform weighting (set the weight $\beta_{pq}$) in such a way that the higher the possibility of the region of interest and the adjacent region being included in the object region is, the larger the weight multiplied by the difference in parallax is. The weight $\beta_{pq}$ of the embodiment can also be calculated by the following expression (7), for example.

$$\alpha_{pq} = \sqrt{L_B(p) \times L_B(q)} \tag{7}$$

Figure 11:
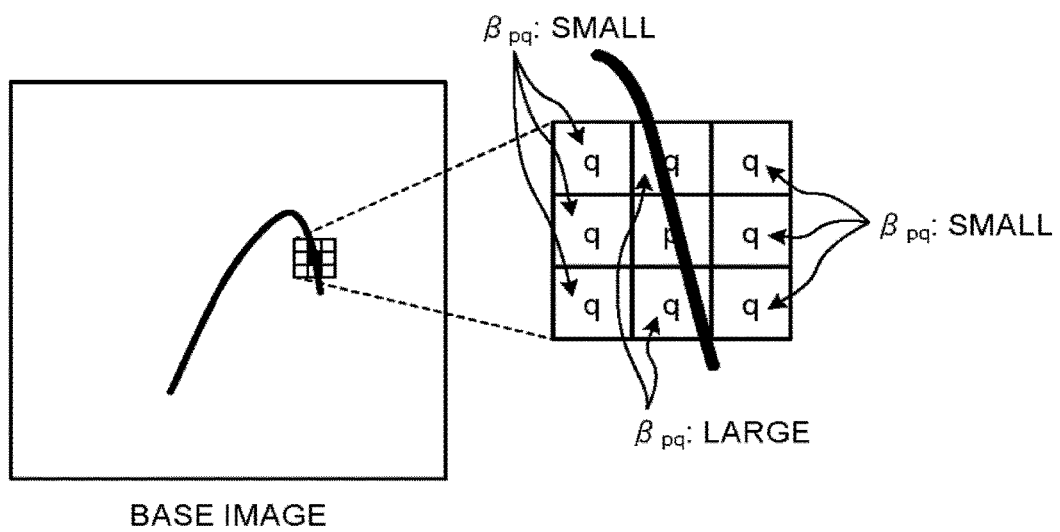
FIG. 11 is a schematic diagram to explain a weight in relation to a degree of continuity of the embodiment.

In expression (7), $L_B(p)$ represents the likelihood of the region of interest while $L_B(q)$ represents the likelihood of the adjacent region. As can be understood from expression (7), the weight $\beta_{pq}$ in relation to the degree of continuity has a large value when the possibility of both of the region of interest and the adjacent region being included in the object region is high. FIG. 11 is a schematic diagram to explain the weight $\beta_{pq}$ in relation to the degree of continuity. In FIG. 11, p represents the region of interest while q represents the adjacent region. In the example of FIG. 11, the region of interest p is included in the object region, and the pixels adjacent to the region of interest p at the upper and the lower sides thereof are the adjacent regions included in the object region. Thus, the weight $\beta_{pq}$ for the adjacent regions is large while the weight $\beta_{pq}$ for the other regions is small.

As described above, the search for the corresponding point of the object region can be performed with high accuracy by preferentially adding the degree of continuity of parallax in the region of interest to the energy (third cost), which is described later. As described above, the likelihood has continuous values from zero to one, thus the weight $\beta_{pq}$ also has continuous values from zero to one. The degree of continuity of parallax is defined as the sum of the multiplication results obtained by multiplying the difference in parallax between the region of interest and each of the multiple regions (adjacent regions) adjacent to the region of interest by the corresponding weight $\beta_{pq}$. The larger the second cost is, the larger the difference in parallax between the region of interest included in the object region and the adjacent region included in the object region is.

Referring back to FIG. 8, to the third cost calculator 306, the first cost is input from the first cost calculator 303 and the second cost is input from the second cost calculator 304. The third cost calculator 306 calculates the third cost on the basis of the first and the second costs. The third cost in the embodiment is obtained by weighted adding of the first cost and the second cost. For example, the third cost can be calculated by the following expression) (8).

$$\text{Third Cost} = \omega \sum_{p \in P} \|T_B(p) - T_R(p')\| \times \alpha_{pp'} + \sum_{p \in P} \sum_{q \in N(p)} \|D(p) - D(q)\| \times \beta_{pq} \tag{8}$$

In expression (8), $\omega$ represents the weight of the first cost. When $\omega$ is set to a large value, the ratio of the first cost to the third cost is increased. For example, when the difference in pixel values between the background region and the object region is large, the ratio between the first and the second costs can be equally evaluated by setting $\omega$ to a small value.

As described above, the second calculator 103 calculates the third cost (energy) based on the first cost indicating the sum of the degrees of similarity corresponding to the respective regions of interest and the second cost indicating the sum of the degrees of continuity of parallaxes corresponding to the respective regions of interest. In this case, the third costs are calculated in number corresponding to the number of combinations of the region of interest and the candidate region.

Referring back to FIG. 5, the selector 104 selects one candidate region for each of the multiple regions of interest in such a way that the third cost (energy) is minimum. Meanwhile, the candidate region selected for each region of interest is determined as the corresponding region of the region of interest. The selector 104 in the embodiment selects the candidate region corresponding to each region of interest when the minimum third cost is calculated by the second calculator 103 as the corresponding region of the region of interest.

The third calculator 105 calculates a three-dimensional position (spatial position) of the region of interest on the basis of the difference in position between the region of interest and the corresponding region. A typical television can restore three-dimensional information from the images taken from different viewpoints.

The setter 106 acquires imaging information about a desired viewpoint position (a viewpoint different from the first and the second viewpoints, in the following description, described as an "intermediate viewpoint" in some cases). The imaging information includes an imaging angle (an arm angle of the X-ray fluoroscopic imaging unit, for example. For example, the setter 106 can also acquire, from the system controller 21, the imaging information corresponding to the intermediate viewpoint. The setter 106 then sets parameters including at least the imaging angle of the X-ray fluoroscopic imaging device. The number of desired viewpoint positions (the number of intermediate viewpoints) can be changed to any number. For example, one or more desired viewpoint positions may be set. For example, when multiple intermediate viewpoints are set, the setter 106 acquires, for each intermediate viewpoint, the imaging information corresponding to the intermediate viewpoint and sets the parameters. In the following description, the imaging direction at the intermediate viewpoint is described as an "intermediate imaging direction" in some cases.

The first generator 107 calculates image coordinates of all of the regions of interest in an image (image corresponding to the intermediate viewpoint) viewed from the intermediate viewpoint on the basis of the spatial positions of the regions of interest obtained by the third calculator 105 and the parameters set by the setter 106, and then produces the image corresponding to the intermediate viewpoint (in the following description, described as an "intermediate image" in some cases). The first generator 107 in the embodiment produces the intermediate image in which only the equipment (an example of the object) such as a guide wire or a catheter is captured. The intermediate image is an image of the object captured in the intermediate imaging direction and corresponds to the "intermediate image" in claims.

The second acquirer 108 acquires the three-dimensional blood vessel image stored in the three-dimensional volume data storage 40.

Figure 12:
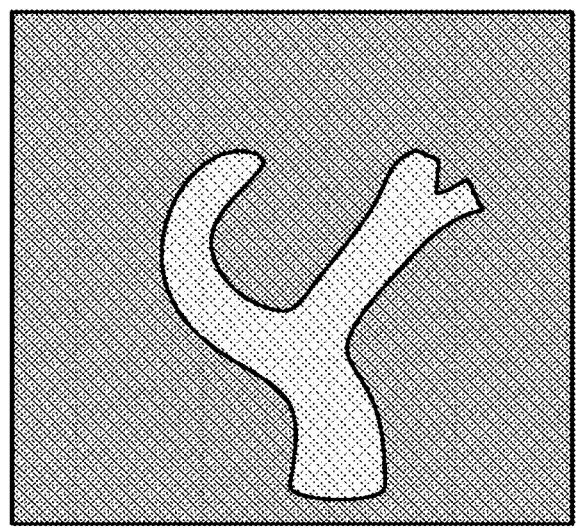
FIG. 12 is a schematic diagram illustrating an example of a rendered blood vessel image of the embodiment.

To the second generator 109, the three-dimensional blood vessel image is input from the second acquirer 108, the information indicating the first and the second viewpoints is input from the first acquirer 101, and the information indicating the intermediate viewpoint is input from the setter 106. The second generator 109 renders (performs volume rendering) the three-dimensional blood vessel image from each of the first viewpoint (first imaging direction), the second viewpoint (second imaging direction), and the intermediate viewpoint (intermediate imaging direction), produces a first rendered blood vessel image corresponding to the first viewpoint (first imaging direction), a second rendered blood vessel image corresponding to the second viewpoint (second imaging direction), and a third rendered blood vessel image corresponding to the intermediate viewpoint (intermediate imaging direction). For rendering the volume data (in this example, the three-dimensional blood vessel image), known various volume rendering techniques can be used. FIG. 12 is a schematic diagram illustrating an example of the first rendered blood vessel image corresponding to the first viewpoint.

Figure 13:
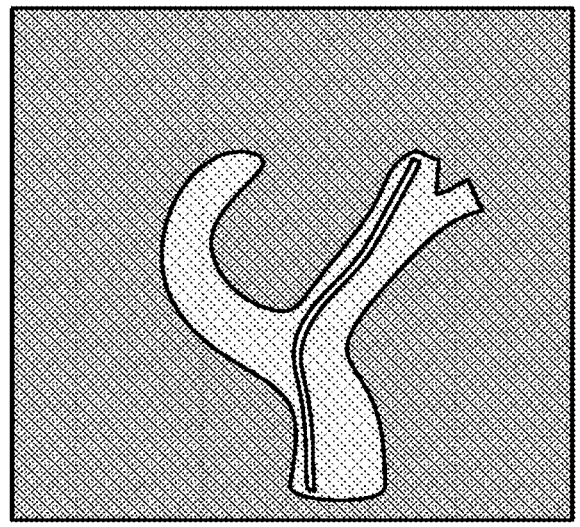
FIG. 13 is a schematic diagram illustrating an example of a first combined image of the embodiment.

The combiner 110 combines the base image and the first rendered blood vessel image produced by the second generator 109 to produce a first combined image. FIG. 13 is a schematic diagram illustrating an example of the first combined image. In a similar manner, the combiner 110 combines the reference image and the second rendered blood vessel image produced by the second generator 109 to produce a second combined image. The combiner 110 combines the intermediate image and the third rendered blood vessel image produced by the second generator 109 to produce a third combined image.

The display controller 111 performs control to display a stereoscopic image including the first, the second, and the third combined images on the display 23. The "stereoscopic image" is an image including a plurality of parallax images having parallax among them. The parallax means a difference in view caused by being viewed from different viewing directions.

The image processor 28 of the embodiment has a hardware configuration including a central processing unit (CPU), a ROM, a RAM, and a communication I/F device, for example. The functions of the respective components of the image processor 28 (the first acquirer 101, the first calculator 102, the second calculator 103, the selector 104, the third calculator 105, the setter 106, the first generator 107, the second acquirer 108, the second generator 109, the combiner 110, and the display controller 111) are implemented by the CPU loading a program stored in the ROM on the RAM and executing the program. The embodiment is not limited thereto. At least part of the functions of the respective components can also be implemented by a hardware circuit (e.g., a semiconductor integrated circuit).

Figure 14:
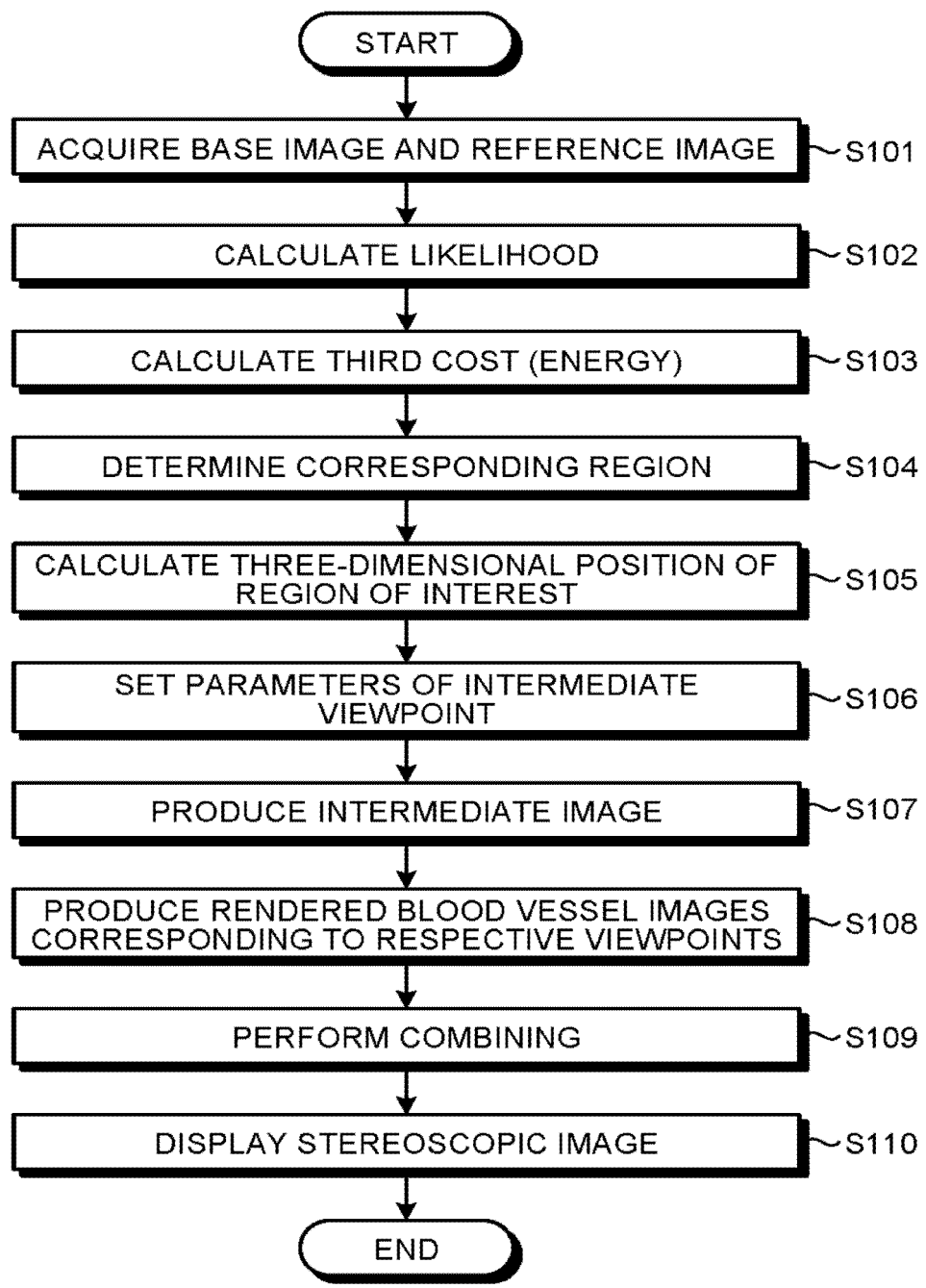
FIG. 14 is a flowchart illustrating an operation example of the image processor of the embodiment.

FIG. 14 is a flowchart illustrating an operation example of the image processor 28 of the embodiment. As illustrated in FIG. 14, the first acquirer 101 acquires the base and the reference images from the subtraction image generator 27 (step S101). The first calculator 102 calculate the likelihood for each of the multiple pixels included in the respective base and reference images on the basis of the pixel value of the pixel (step S102) and produces the likelihood maps. The second calculator 103 calculates the third cost (energy) on the basis of the base and the reference images acquired at step S101 and the likelihood maps produced at step S102 (step S103). The selector 104 selects the candidate regions respectively corresponding the regions of interest in such a way that the third cost is minimum, and determines the corresponding regions of the respective regions of interest (step S104).

The third calculator 105 calculates the three-dimensional position (spatial position) of the region of interest on the basis of the difference in position between the region of interest and the corresponding region (step S105. The setter 106 sets the parameters (including at least the imaging angle) of a desired viewpoint (intermediate viewpoint) (step S106). The first generator 107 produces the intermediate image on the basis of the partial position obtained at step S105 and the parameters set at step S106 (step S107). The second generator 109 renders the three-dimensional blood vessel image from the respective viewpoints (the first, the second, and the intermediate viewpoints) and produces the rendered blood vessel images corresponding to the respective viewpoints (in this example, the first, the second, and the third rendered blood vessel images) (step S108. The combiner 110 performs the combining processing (step S109). As described above, the combiner 110 of the embodiment produces the first combined image by combining the base image and the first rendered blood vessel image. The combiner 110 produces the second combined image by combining the reference image and the second rendered blood vessel image. The combiner 110 produces the third combined image by combining the intermediate image and the third rendered blood vessel image.

The display controller 111 performs the control to display the stereoscopic image including the combined image (parallax image) obtained by the combining processing step S109 on the display 23 (step S110).

As described above, in the embodiment, the corresponding point search the object region can be performed with high accuracy by preferentially reflecting the degree of similarity of the region of interest having a high possibility of being included in the object region on the third cost and the degree of continuity of parallax in the object region in the third cost. The corresponding point of the object region thus obtained with high accuracy makes it possible to produce the parallax image of the object corresponding to another viewpoint (a desired viewpoint different from the first and the second viewpoints) with high accuracy. When the instrument such as a catheter is intended to be viewed in a stereoscopic manner as the object in the PCI treatment, for example, the structure of the embodiment is particularly effective.

The configuration of the embodiment is also applicable to when the instrument such as a catheter is viewed in a stereoscopic manner in the PCI treatment where the instrument such as a guide wire or the catheter is inserted into a blood vessel of an unmoving organ such as a brain and a narrowed portion or a clogged portion of the blood vessel is widened besides when the instrument such as a catheter is viewed in a stereoscopic manner as the object in the PCI treatment where the instrument such as the guide wire or the catheter inserted into a coronary artery of a heart and a narrowed portion or a clogged portion of the coronary artery is widened. The configuration of the embodiment is also applicable to CV-3D (trademark) that restructures a three-dimensional blood vessel image from a plurality of vessel angiograms collected at different angles and provides vessel measurement results (e.g., a vessel length, a vessel diameter, a vasoconstriction rate, and a brunch angle) on the basis of the restructured three-dimensional blood vessel image, for example.

Modifications

The following describes modifications. The following modifications can be arbitrarily combined.

(1) First Modification

Figure 15:
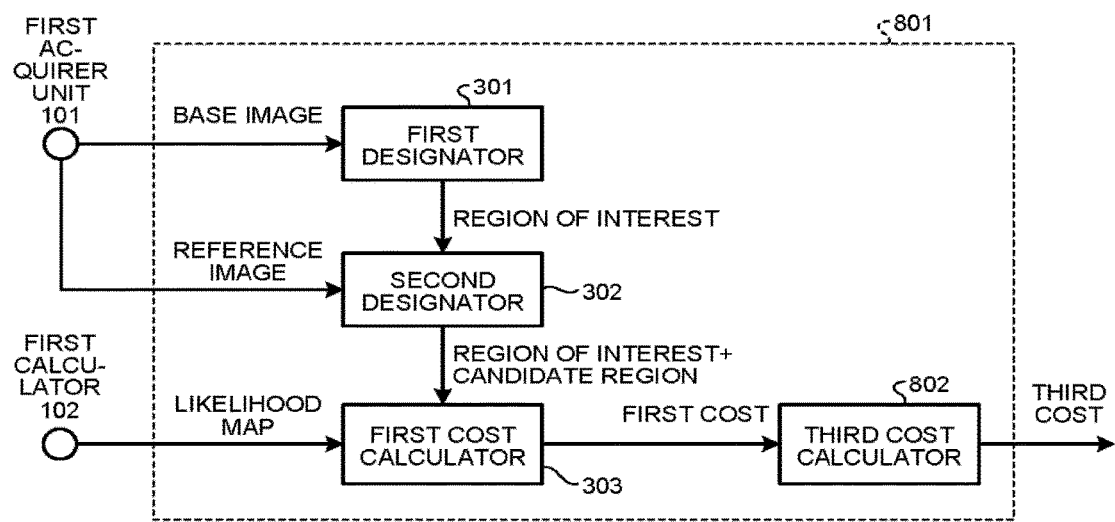
FIG. 15 is a schematic diagram illustrating an example of a detailed structure of a second calculator of a modification

In the calculation of the third cost, the degree continuity of parallax may not be taken into consideration, for example. As illustrated in FIG. 15, a second calculator 801 may be configured to include the first designator 301, the second designator 302, the first cost calculator 303, and a third cost calculator 802, but not include the second cost calculator 304 or the storage 305. To the third cost calculator 802, the first cost is input from the first cost calculator 303. The third cost calculator 802 calculates the third cost on the basis of the first cost. For example, the third cost calculator 802 can also calculate the input first cost as the third cost.

(2) Second Modification

In the embodiment, the X-ray diagnostic apparatus having a function of displaying a 3D load map image is described as an example of the stereoscopic image display apparatus. The stereoscopic image display apparatus is not limited to this example.

The embodiment is applicable to the stereoscopic image display apparatus using a chroma key technique in which a portion in a specific color (e.g., blue) included in an image is replaced with another image, for example. For example, when an object such as a person is imaged, a plurality of images are taken from a plurality of viewpoints using a blue background (blue back) such as blue cloth, and any one of the images can be used as the base image and the other images than the base image can be used as the reference images (in addition, an image corresponding to another viewpoint can also be prepared). In this case, in a similar manner as the embodiment described above, the corresponding point search of the object region can be performed with high accuracy by preferentially reflecting the degree of similarity of the region of interest having a high possibility of being included in the object region and the degree of continuity of parallax in the object region on the third cost. The corresponding point of the object region thus obtained with high accuracy makes it possible to produce a parallax image of the object (e.g., a person present in front of the blue back) corresponding to another viewpoint with high accuracy. As a result, a viewer who views the stereoscopic image display apparatus can preferably view the object such as person present in a region excluding the background in a stereoscopic manner.

Program

The program executed by the image processor 28 may be stored in a computer connected to a network such as the Internet and provided by being downloaded through the network. The program executed by the image processor 28 may be provided or distributed through a network such as the Internet. The program executed by the image processor 28 may be preliminarily embedded and provided in a nonvolatile recording medium such as a ROM).

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An image processing apparatus, comprising:
   first acquisition circuitry that acquires a first image of an object captured in a first imaging direction and a second image of the object captured in a second imaging direction different from the first imaging direction;
   first calculation circuitry that calculates, for each pixel of a plurality of pixels included in the respective first and second images, a likelihood of whether the pixel is included in a region of the object on the basis of feature information indicating image feature;
   second calculation circuitry that calculates, based on the likelihood, a degree of similarity between a region of interest in the first image and a candidate region in the second image, the candidate region being a candidate of a corresponding region corresponding to the region of interest in the first image; and
   selection circuitry that selects the candidate region in the second image serving as the corresponding region based on the degree of similarity.

2. The apparatus according to claim 1, wherein the second calculation circuitry calculates the degree of similarity by weighting a difference in pixel value between the region of interest and the candidate region based on the calculated likelihood.

3. The apparatus according to claim 2, further comprising:
   first designation circuitry that designates a plurality of regions of interest included in the first image; and
   second designation circuitry that designates, as a plurality of candidate regions corresponding to the designated regions of interest in the first image, a plurality of regions present on an epipolar line in the second image, the epipolar line being determined based on a position of the region of interest in the first image, wherein
   the second calculation circuitry calculates a third cost based on a first cost that indicates a sum of the degrees of similarity corresponding to the respective regions of interest, and
   the selection circuitry selects one candidate region for each of the plurality of regions of interest in such a way that the third cost is minimum.

4. The apparatus according to claim 2, wherein the second calculation circuitry further performs the weighting in such a way that a higher a probability of the region of interest being included in the region of the object is, the larger a weight to be multiplied by the difference in pixel value is.

5. The apparatus according to claim 2, wherein the second calculation circuitry further performs the weighting in such a way that a higher a probability of both of the region of interest and the candidate region being included in the region of the object is, the smaller a weight to be multiplied by the difference in pixel value is.

6. The apparatus according to claim 1, wherein
   the second calculation circuitry further calculates a degree of continuity of parallax by weighting a difference in parallax between the region of interest and an adjacent region, which is a region adjacent to the region of interest based on the likelihood, and
   the selection circuitry further selects the candidate region serving as the corresponding region based on the calculated degree of similarity and the calculated degree of continuity.

7. The apparatus according to claim 6, further comprising:
   first designation circuitry that designates a plurality of regions of interest included in the first image; and
   second designation circuitry that designates, as a plurality of candidate regions corresponding to the regions of interest, a plurality of regions present on an epipolar line in the second image, the epipolar line being determined band on a position of the region of interest in the first image, wherein
   the second calculation circuitry further calculates a third cost based on a first cost indicating a sum of the degrees of similarity corresponding to the respective regions of interest and a second cost indicating a sum of the degrees of continuity corresponding to the respective regions of interest, and the selection circuitry further selects one candidate region for each of the plurality of regions of interest in such a way that the third cost is minimum.

8. The apparatus according to claim 6, wherein the second calculation circuitry further performs the weighting in such a way that A higher a probability of both of the region of interest and the candidate region being included in the region of the object is, the larger a weight to be multiplied by the difference in parallax is.

9. The apparatus according to claim 1, wherein
the object is an instrument to be inserted into a blood vessel,
the first image is a subtraction image between an image based on projection data obtained by performing X-ray fluoroscopy on a subject in a state where the object is not inserted into a blood vessel in the first imaging direction and another image based on projection data obtained by performing the X-ray fluoroscopy on the subject in a state where the object is inserted into the blood vessel in the first imaging direction, and
the second image is a subtraction image between an image based on projection data obtained by performing the X-ray fluoroscopy on the subject in the state where the object is not inserted into the blood vessel in the second imaging direction and another image based on projection data obtained by performing the X-ray fluoroscopy on the subject in the state where the object is inserted into the blood vessel in the second imaging direction.

10. The apparatus according to claim 9, further comprising:
third calculation circuitry that calculates a three-dimensional position of the region of interest based on a difference in position between the region of interest and the corresponding region;
set circuitry that sets parameters including at least an imaging angle of an X-ray fluoroscopic imaging device that produces the projection data by performing the X-ray fluoroscopy on the subject;
first generation circuitry that produces an intermediate image indicating the subtraction image corresponding to an intermediate imaging direction different from the first imaging direction and the second imaging direction based on the three-dimensional position and the parameters;
second acquisition circuitry that acquires a three-dimensional blood vessel image indicating volume data of the blood vessel in the state where the object is not inserted into the blood vessel;
second generation circuitry that renders the three-dimensional blood vessel image from the first imaging direction, the second imaging direction, and the intermediate imaging direction and produces a first rendered blood vessel image corresponding to the first imaging direction, a second rendered blood vessel image corresponding to the second imaging direction, and a third rendered blood vessel image corresponding to the intermediate imaging direction;
combination circuitry that produces a first combined image by combining the first image and the first rendered blood vessel image, a second combined image by combining the second image and the second rendered blood vessel image, and a third combined image by combining the intermediate image and the third rendered blood vessel image; and
display control circuitry that performs control to display a stereoscopic image including the first combined image, the second combined image, and the third combined image on a display.

11. An image processing method, comprising:
acquiring a first image of an object captured in a first imaged direction and a second image of the object captured in a second imaging direction different from the first imaging direction;
calculating, for each pixel of a plurality of pixels included in the respective first and second images, a likelihood of whether the pixel is included in a region of the object based on feature information indicating image feature;
calculating, based on the likelihood, a degree of similarity between a region of interest in the first image and a candidate region in the second image, the candidate region being a candidate of a corresponding region corresponding to the region of interest in the first image; and
selecting the candidate region in the second image serving as the corresponding region based on the degree of similarity.

12. A non-transitory computer-readable medium containing an image processing program that causes a computer to perform:
acquiring a first image of an object captured in a first imaged direction and a second image of the object captured in a second imaging direction different from the first imaging direction;
calculating, for each pixel of a plurality of pixels included in the respective first and second images, a likelihood of whether the pixel is included in a region of the object based on feature information indicating image feature;
calculating, based on the likelihood, a degree of similarity between a region of interest in the first image and a candidate region in the second image, the candidate region being a candidate of a corresponding region corresponding to the region of interest in the first image; and
selecting the candidate region in the second image serving as the corresponding region based on the degree of similarity.

13. A stereoscopic image display apparatus, comprising:
a display that displays a stereoscopic image including a plurality of parallax images;
first acquisition circuitry that acquires a first image of an object captured in a first imaging direction and a second image of the object captured in a second imaging direction different from the first imaging direction;
first calculation circuitry that calculates, for each pixel of a plurality of pixels included in the respective first and second images, a likelihood of whether the pixel is included in a region of the object based on feature information indicating image feature;
second calculation circuitry that calculates, based on the likelihood, a degree of similarity between a region of interest in the first image and a candidate region in the second image, the candidate region being a candidate of a corresponding region corresponding to the region of interest in the first image;
selection circuitry that selects the candidate region in the second image serving as the corresponding region based on the degree of similarity;
third calculation circuitry that calculates a three-dimensional position of the region of interest based on a difference in position between the region of interest and the corresponding region;

set circuitry that sets parameters including at least an imaging angle of an imaging device that captures the object;

generation circuitry that produces an intermediate image of the object captured in an intermediate imaging direction different from the first imaging direction and the second imaging direction based on the three-dimensional position and the set parameters; and display control circuitry that performs control to display the stereoscopic image including the first image, the second image, and the intermediate image on the display.

\* \* \* \* \*